US009033940B2

(12) United States Patent
Muri et al.

(10) Patent No.: US 9,033,940 B2
(45) Date of Patent: May 19, 2015

(54) EYE TREATMENT SYSTEM WITH FLUIDICS PUMP INTERFACE

(75) Inventors: John I. Muri, Aliso Viejo, CA (US); Craig Edwards, Mission Viejo, CA (US)

(73) Assignee: Abbott Medical Optics Inc., Santa Ana, CA (US)

( * ) Notice: Subject to any disclaimer, the term of this patent is extended or adjusted under 35 U.S.C. 154(b) by 1283 days.

(21) Appl. No.: 11/558,416

(22) Filed: Nov. 9, 2006

(65) Prior Publication Data

US 2008/0114312 A1 May 15, 2008

(51) Int. Cl.
| | |
|---|---|
| *A61M 35/00* | (2006.01) |
| *F04B 43/12* | (2006.01) |
| *A61M 1/00* | (2006.01) |
| *A61M 31/00* | (2006.01) |
| *A61M 5/20* | (2006.01) |
| *A61F 9/007* | (2006.01) |
| *A61M 5/142* | (2006.01) |

(52) U.S. Cl.
CPC .......... *F04B 43/1253* (2013.01); *A61F 9/00745* (2013.01); *A61M 1/0058* (2013.01); *A61M 5/14232* (2013.01); *A61M 2205/123* (2013.01); *A61M 2205/3331* (2013.01); *A61M 2205/505* (2013.01); *A61M 2205/52* (2013.01); *A61M 2210/0612* (2013.01)

(58) Field of Classification Search
CPC ....... A61M 35/00; A61M 1/00; A61M 31/00; A61M 5/20
USPC ......................................... 604/294, 295, 541
See application file for complete search history.

(56) References Cited

U.S. PATENT DOCUMENTS

| | | | | |
|---|---|---|---|---|
| 4,187,057 A | * | 2/1980 | Xanthopoulos | 417/63 |
| 4,627,833 A | * | 12/1986 | Cook | 604/34 |

(Continued)

FOREIGN PATENT DOCUMENTS

| | | |
|---|---|---|
| DK | WO 00/70225 | 11/2000 |
| WO | WO 93/17729 | 11/2006 |

*Primary Examiner* — Tatyana Zalukaeva
*Assistant Examiner* — Ilya Treyger
(74) *Attorney, Agent, or Firm* — Abbott Medical Optics Inc.

(57) ABSTRACT

An eye treatment system for performing an ocular surgical procedure contains an eye treatment probe or handpiece, a treatment console, an eye treatment cassette, and a pump formed by the engagement of the treatment cassette with the treatment console. The handpiece is configured to provide at least irrigation fluid to, and aspiration of fluid from, a subject eye. The treatment console comprises a controller configured to control the eye treatment probe. The eye treatment cassette engages the treatment console to couple the eye treatment probe with the treatment console. The pump comprises a pump head having a plurality of projections disposed to rotate about an axis, a ramp disposed near the rotating projections, and a resilient channel configured to transfer fluid when engaged by the ramp and the plurality of projections. The ramp is configured to reduce pressure fluctuations with the eye during a surgical procedure and comprises and entrance portion, a central portion, and an exit portion. The entrance portion has an arcuate extent over which the projections close the channel as the head rotates. The central portion has an arcuate extent over which the channel is sealed by the projections as the head rotates. The exit portion has an arcuate extent over which the projections open the channel as the head rotates. The ramp is configured such that the arcuate extent of the entrance portion is unequal to the arcuate extent of the exit portion.

11 Claims, 11 Drawing Sheets

(56) References Cited

U.S. PATENT DOCUMENTS

| | | | |
|---|---|---|---|
| 4,758,238 A * | 7/1988 | Sundblom et al. | 604/319 |
| 4,920,336 A | 4/1990 | Meijer | |
| 5,125,891 A | 6/1992 | Hossain et al. | |
| 5,195,960 A | 3/1993 | Hossain et al. | |
| 5,230,614 A | 7/1993 | Zanger et al. | |
| 5,454,783 A | 10/1995 | Grieshaber et al. | |
| 5,470,211 A | 11/1995 | Knott et al. | |
| 5,499,969 A * | 3/1996 | Beuchat et al. | 604/30 |
| 5,549,461 A | 8/1996 | Newland | |
| 5,676,530 A | 10/1997 | Nazarifar | |
| 5,693,020 A | 12/1997 | Rauh | |
| 5,747,824 A | 5/1998 | Jung et al. | |
| 6,902,542 B2 * | 6/2005 | Gordon | 604/35 |
| 6,962,488 B2 | 11/2005 | Davis et al. | |
| 7,070,578 B2 | 7/2006 | Leukanech et al. | |
| 7,214,038 B2 * | 5/2007 | Saxer et al. | 417/477.2 |
| 2003/0108429 A1 | 6/2003 | Angelini et al. | |
| 2004/0037724 A1 | 2/2004 | Haser et al. | |
| 2005/0069419 A1 | 3/2005 | Cull et al. | |

\* cited by examiner

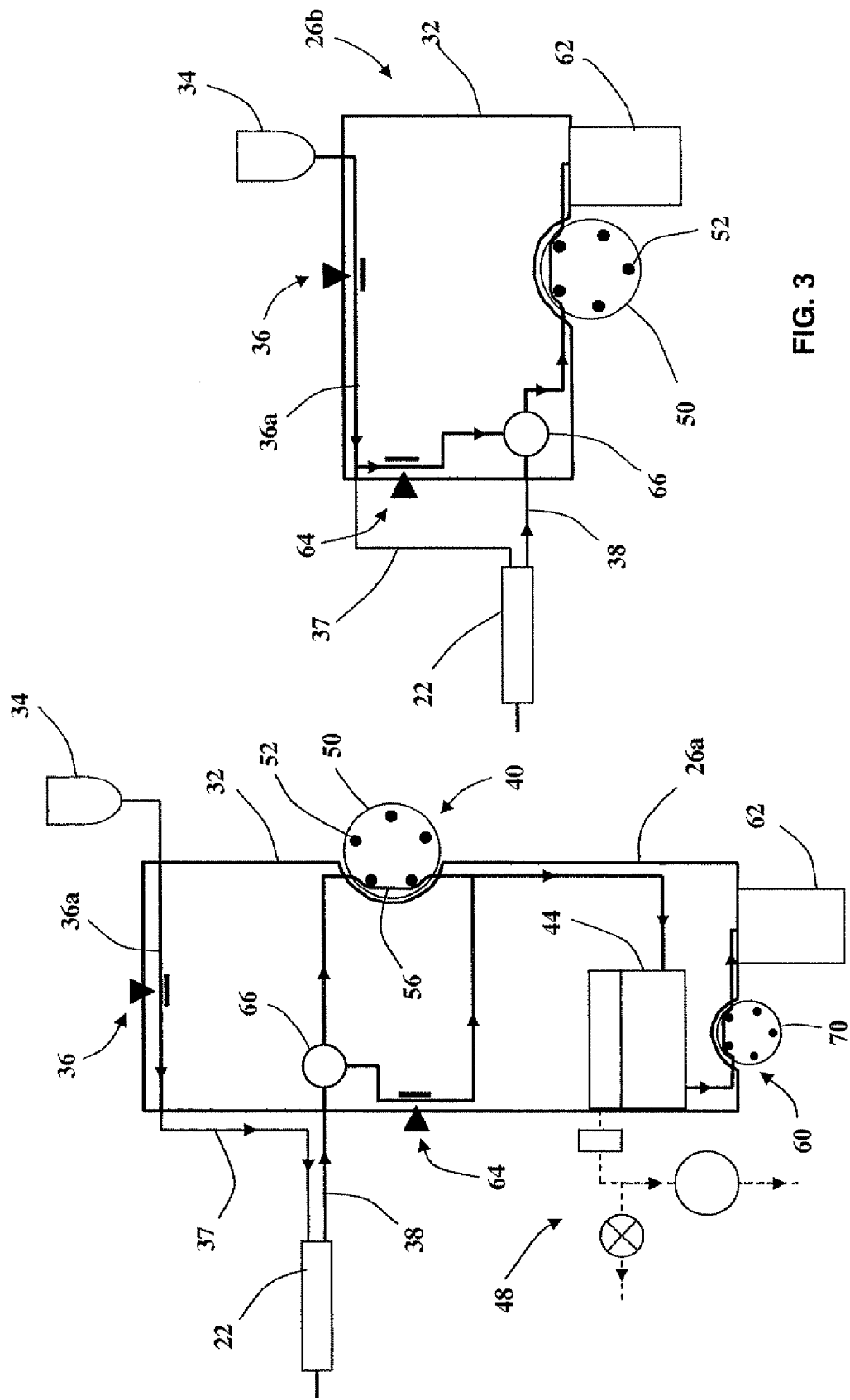

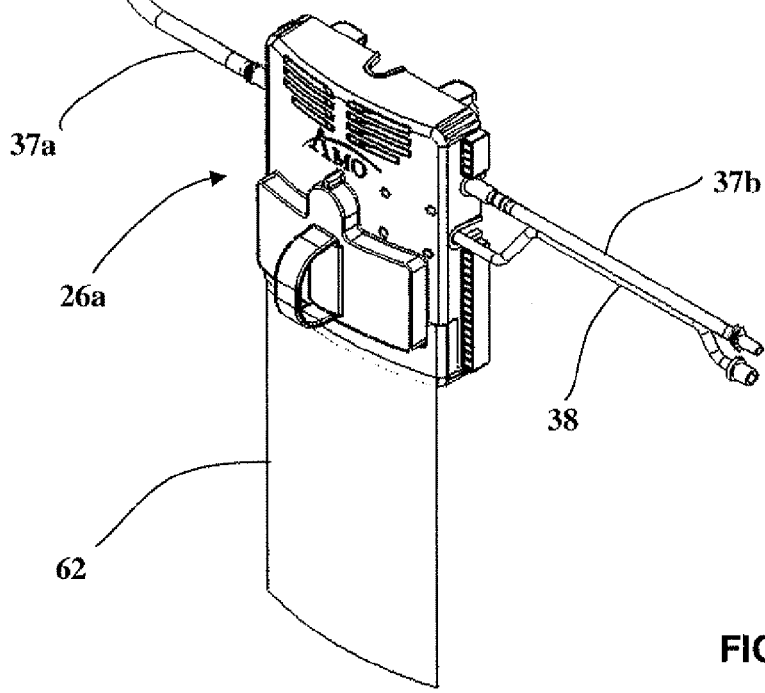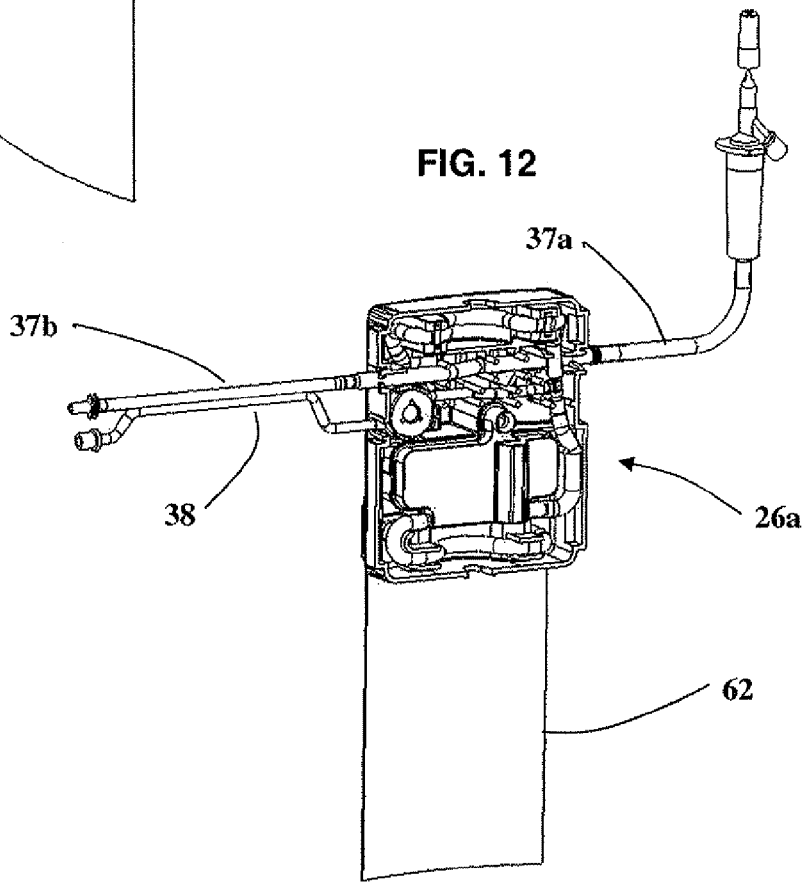

EYE TREATMENT SYSTEM WITH FLUIDICS PUMP INTERFACE

BACKGROUND OF THE INVENTION

1. Field of the Invention

This invention relates generally to an eye treatment system, and more specifically to an eye treatment system with an advanced fluidics pump interface.

2. Description of the Related Art

Volumetric pumps such as peristaltic pumps are used to remove fluid and other material from a surgical site. For example, in ophthalmic surgical systems, volumetric pumps may be used to precisely regulate the flow of fluid from the eye during a cataract, vitrectomy, or other surgical procedure. Because of the sterile environment necessitated by these procedures, portions of the pump and other components of the fluidic system, such as valves and sensors, may be configured within a disposable and/or separable fluidics cassette that is replaced or separately sterilized after a surgery.

In the case of a peristaltic pump, several fingers or rollers are circularly disposed within a pump head that rotates such that the fingers successively engage a tubing portion through which a fluid is pumped. As the fingers engage the tubing portion, fluid within a volume of the tubing is entrapped between successive pairs of rollers and so transferred from an inlet of the pump to an outlet.

One problem encountered with peristaltic and other volumetric pumps is that as each finger of the pump initially engages the tubing portion, compression of the tubing portion produces a localized pressure variation that is subsequently transmitted upstream to a surgical handpiece and into the eye as a pressure wave. If the pressure fluctuation is too large or sudden, damage to the eye may result.

Various approaches to dealing with unwanted pressure fluctuations produced by peristaltic and other types of volumetric pumps have been proposed, including those disclosed in U.S. Pat. Nos. 5,230,614 and 6,962,488, which are herein incorporated by reference. While these solutions may work in some surgical systems, other systems place more demanding challenges to the mitigation of pressure fluctuation. Such demands include tight cassette packaging constraints, the use of multiple pumps in a single cassette, or orientation of the pump within the cassette.

Because of the increasing demands produced by advances surgical and other fluidics systems, there is a need for more advanced solutions in mitigating the occurrence of pressure fluctuations produced by volumetric pumps.

BRIEF DESCRIPTION OF THE DRAWINGS

Embodiments of the present invention may be better understood from the following detailed description when read in conjunction with the accompanying drawings. Such embodiments, which are for illustrative purposes only, depict the novel and non-obvious aspects of the invention. The drawings include the following listed figures:

FIG. 2 is a block diagram of portions of a surgical system according to embodiments of the invention including two volumetric pumps and a vacuum system.

FIG. 3 is a block diagram of portions of a surgical system according to embodiments of the invention including one volumetric pump and a vacuum system.

FIG. 11 is a front perspective view of the cassette shown in FIG. 4.

FIG. 12 is a rear perspective view of the cassette shown in FIG. 4.

DETAILED DESCRIPTION OF THE DRAWINGS

The present invention is generally directed to systems utilizing volumetric pumps configured to reduce or eliminate pressure fluctuations at the pump entrance. Embodiments of the present invention may find particular use in eye treatment systems where pressure fluctuations at the pump entrance can be propagated upstream to eye, potentially resulting in unwanted damages. Without wishing to limit the scope thereof, embodiments of the present invention will be discussed with regard to a system for treating an eye of a patient. It will be appreciated that embodiments of the invention may also be applied to other systems, including other surgical system for use in performing procedures on other parts of the body of a subject.

Figure 1:
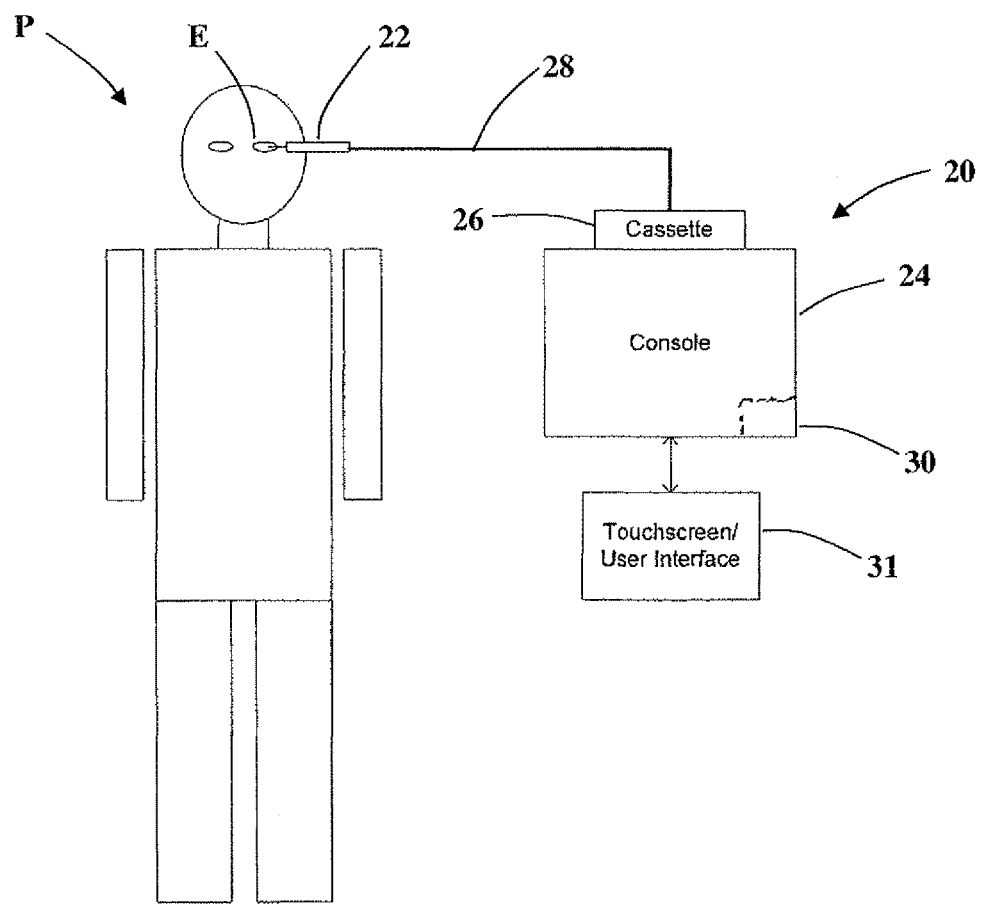
FIG. 1 is system diagram of a surgical system for use on the eye of a subject according to embodiments of the invention.

Referring to FIG. 1, a surgical system 20 generally comprises an eye treatment probe or handpiece 22 that is coupled to a console 24 by a cassette 26 configured to supply irrigation and aspiration functions to the handpiece 22. Handpiece 22 generally includes a handle or gripping portion for manually manipulating and supporting an insertable probe tip. The probe tip includes a distal end that is insertable into an eye E of a patient P, with one or more lumens in the probe tip allowing irrigation fluid to flow into the eye E. Aspiration fluid may also be withdrawn through a lumen of the probe tip, with the console 24 and/or the cassette 26 generally including a vacuum aspiration source, a positive displacement or volumetric aspiration pump, or both. Flexible conduits 28 of the cassette 26 help avoid direct contact between irrigation and aspiration fluids flowing to or from the eye and the components of console 24.

When the distal end of the probe tip of handpiece 22 is inserted into the eye E, an electrical conductor and/or pneumatic line (not shown) may also be provided between the console 24 and the handpiece 22. For example, to enable phacoemulsification of the natural lens in the eye E, an electrical line may be included to provide power from the console 24 to drive a piezoelectric device located in the handpiece 22. This piezoelectric device helps to fragment the tissue of the lens, which can then be drawn into a port of the tip by aspiration flow. In other embodiments, the handpiece 22 is configured to remove vitreous material in the posterior chamber of the eye E, for example, by including an electrically or pneumatically driven cutter blade. In any case, a controller 30 in the console 24 is generally included to control the volume of material removed by the aspiration flow, regulate irrigation flow through handpiece 22 (or a separate probe structure), manage electrical and/or pneumatic drivers connected to the handpiece 22, and/or receive one or more input signals from sensors for monitoring the state of the system 20 during a surgical procedure.

The controller 30 may include an embedded micro-controller and/or many of the components typically found a personal computer, such as a micro-processor, data bus, memory chips, input devices, and/or output drivers. The controller 30 may also include a user interface 31 and/or a foot pedal input device (not shown), and the like. Controller 30 may generally include hardware, firmware, and/or software capabilities, with the software and/or firmware typically comprising machine readable code or programming instructions for implementing one, some, or all of the methods described herein. The code may be embodied by a tangible media such as a memory, a magnetic recording media, an optical recording media, or the like. Controller 30 may have (or be coupled to) a recording media reader, or the code may be transmitted to controller 30 by a network connection such as an internet, an intranet, an Ethernet™, a wireless network, or the like. Along with programming code, controller 30 may include stored data or correlations for implementing the methods described herein, and may generate and/or store data that records parameters corresponding to the treatment of one or more patients. Many components of console 24 may be found in or modified from known commercial phacoemulsification systems from Advanced Medical Optics Inc. of Santa Ana, Calif.; Alcon Manufacturing, Ltd. of Fort Worth, Tex.; Bausch and Lomb of Rochester, N.Y.; and other suppliers.

FIG. 2 is a schematic representation of a cassette 26a according to an embodiment of the invention that is disposed within a cassette frame, housing, or body 32 and having elements that interface with the console 24, for example, to couple the console 24 to the handpiece 22. An irrigation bottle, container, or source 34 may be used to provide irrigation fluid pressure, for example, by relying at least in part on a gravity pressure head that varies with a height of the irrigation source 34 or the like. An irrigation on/off pinch valve 36 may include a short segment of a resilient flexible conduit 36a within the cassette 26a, which can be engaged and actuated by an actuator of the console 24. A surface of the cassette body 32 may be disposed opposite the actuator to facilitate closure of the conduit segment. Alternative irrigation flow systems might include pumps, alternative fluid pressurization drive systems, fluid pressure or flow modulating valves, and/ or the like. Regardless, the irrigation network generally defines an irrigation fluid conduit path or line 37 between irrigation source 34 and an irrigation port on the insertable probe tip of handpiece 22. In some embodiments, irrigation fluid from the irrigation source 34 is additionally or alternatively provided to a separate handpiece (not shown) that is different from the handpiece 22.

Aspiration of fluid and other matter from the eye E through an aspiration line 38 may be provided, in conjunction with the cassette 26a, by either a volumetric or peristaltic pump 40 and/or a holding tank 44 to which a vacuum is applied via a vacuum source 48. Alternatively, the vacuum source 48 may be directly coupled to the aspiration line 38. In any case, the vacuum source 48 may comprise a Venturi pump and/or a rotary vane pump; however, other types of pumps or other vacuum sources (e.g., a vacuum line) may be used in order to produce a desired vacuum level in the holding tank 44. In some embodiments, other types of pumps may be used to provide aspiration capabilities to the handpiece 22, for example, a hybrid pump, such as the Concentrix pump by Bausch & Lomb, may be provided that may incorporate capabilities of both a vacuum pump and a flow pump.

In the illustrated embodiment, the peristaltic pump 40 is formed by engagement of the cassette 26a with a pump head 50, which may be part of the console 24. The pump head 50 includes one or more rotating projections, fingers, or rollers 52 disposed about an axis and near a ramp 54 that may be molded or attached to the cassette body 32. The pump head 50 may be formed within or attached to the cassette body 32. Fluid transfer by the peristaltic pump 40 is produced as a resilient channel 56, in fluid communication with the aspiration line 38, is engaged by or squeezed between the ramp 54 and one or more of the projections 52. The resilient channel 56 may be a portion of a tube made of a polymer or other suitable material. Alternatively, the resilient channel 56 may be part of a molded channel and/or a gland that is squeezed or compressed during operation of the peristaltic pump 40. As described in greater detail below, the ramp 54 may be configured according to embodiments of the invention to reduce pressure variations within the aspiration line 38 that can be produced when the resilient channel 56 is initially engaged by the protrusions 52. Fluid aspirated through the handpiece 22 may be deposited in the holding tank 44, regardless of whether the peristaltic pump 40 or the vacuum source 48 is used. A second volumetric or peristaltic pump 60 may be configured as a drain pump that intermittently transfers fluid from the holding tank 44 to a waste bag 62.

During operation, a selector valve 64 may be used to select the source of aspiration for the handpiece 22. When the valve 64 is closed, the peristaltic pump 40 may be used for producing aspiration flow from the handpiece 22, generally independent of the pressure in the holding tank 44. Alternatively, the vacuum source 48 may be used in conjunction with the holding tank 44 to produce aspiration flow by opening the valve 64 and halting rotation of the peristaltic pump 40. When peristaltic pump 40 is not being operated, at least one of the protrusions 52 pinches off the arcuate resilient channel 56, thus preventing aspiration flow therethrough. Material is instead drawn into an aspiration port of handpiece 12 via the vacuum source 48 through the open valve 64. In this operational mode, the aspiration port draws fluid therein based on the pressure differential between holding tank 44 and the chamber of the eye E in which the fluid port is disposed. A pressure sensing device or vacuum sensor 66 may be used to determine or estimate an aspiration pressure, flow rate, line deformation, or the like, and to adjust operation of the peristaltic pump 40 and/or the vacuum source 48 so as to maintain a predetermined flow rate or pressure level at the vacuum sensor 66 or elsewhere within the system. In some embodiments, the vacuum sensor 66 is coupled to the console 24 to provide a pressure sensing mechanism providing an output that is used by the controller 30 to control one or more aspects of the system 20.

Referring to FIG. 3, in some embodiments, a cassette 26b comprises only the single peristaltic pump 40, which is available for providing aspiration through the handpiece 22. In the illustrated embodiments of FIGS. 2 and 3, the cassettes 26a and 26b may use a common cassette body 32 and various other components used in both configurations (e.g., the vacuum sensor 66). When the cassette 26b is in this configuration, the valve 64 may be used provide venting or reflux to the handpiece 22. When the valve 64 is open, an equalization pressure is provided between the irrigation and aspiration lines 37, 38, for example during an occlusion of the aspiration tip of the handpiece 22.

Figure 4:
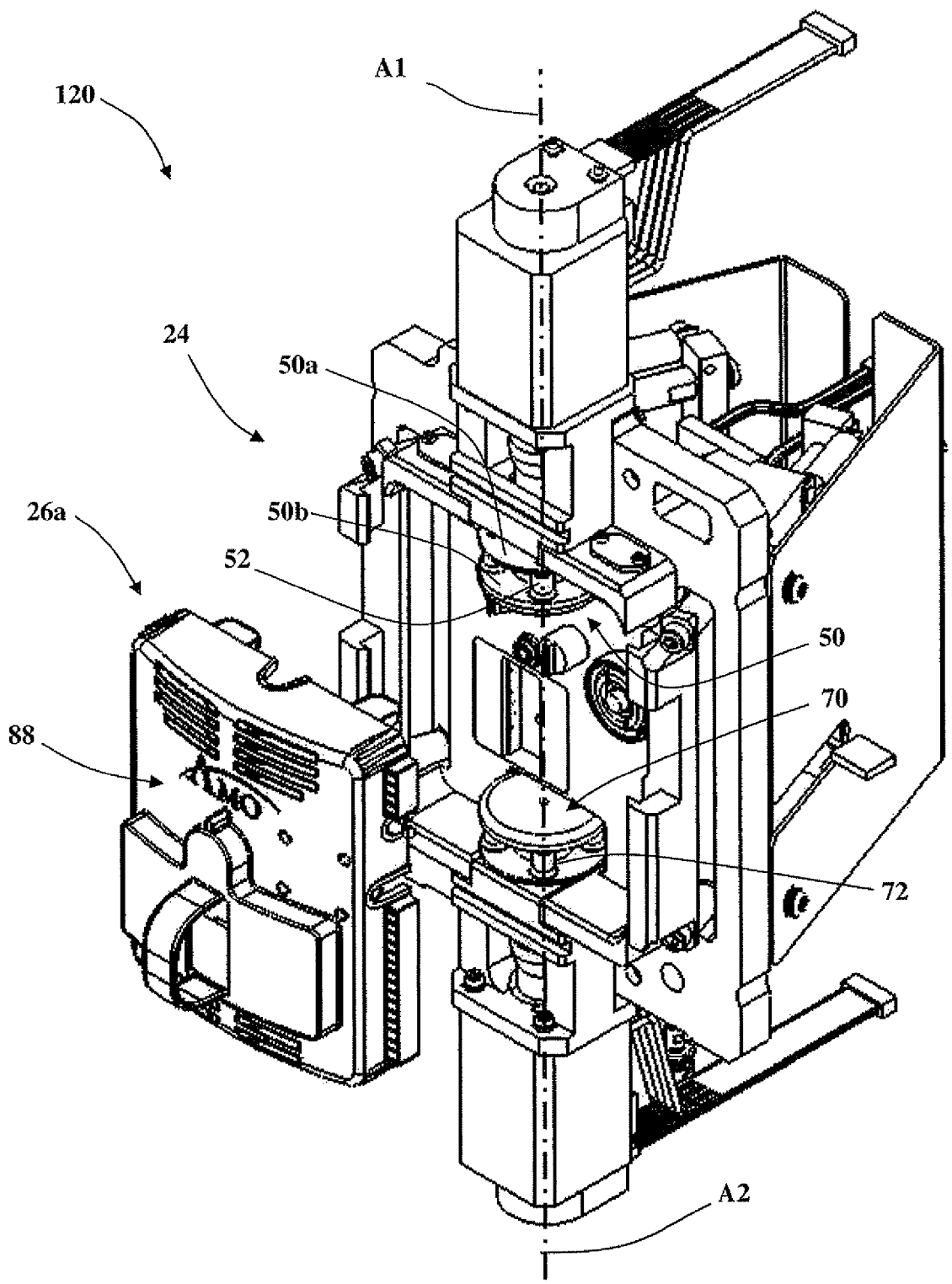
FIG. 4 is a perspective view of the surgical system illustrated in FIG. 2 showing a fluidics cassette separated from a surgical console.
Figure 5:
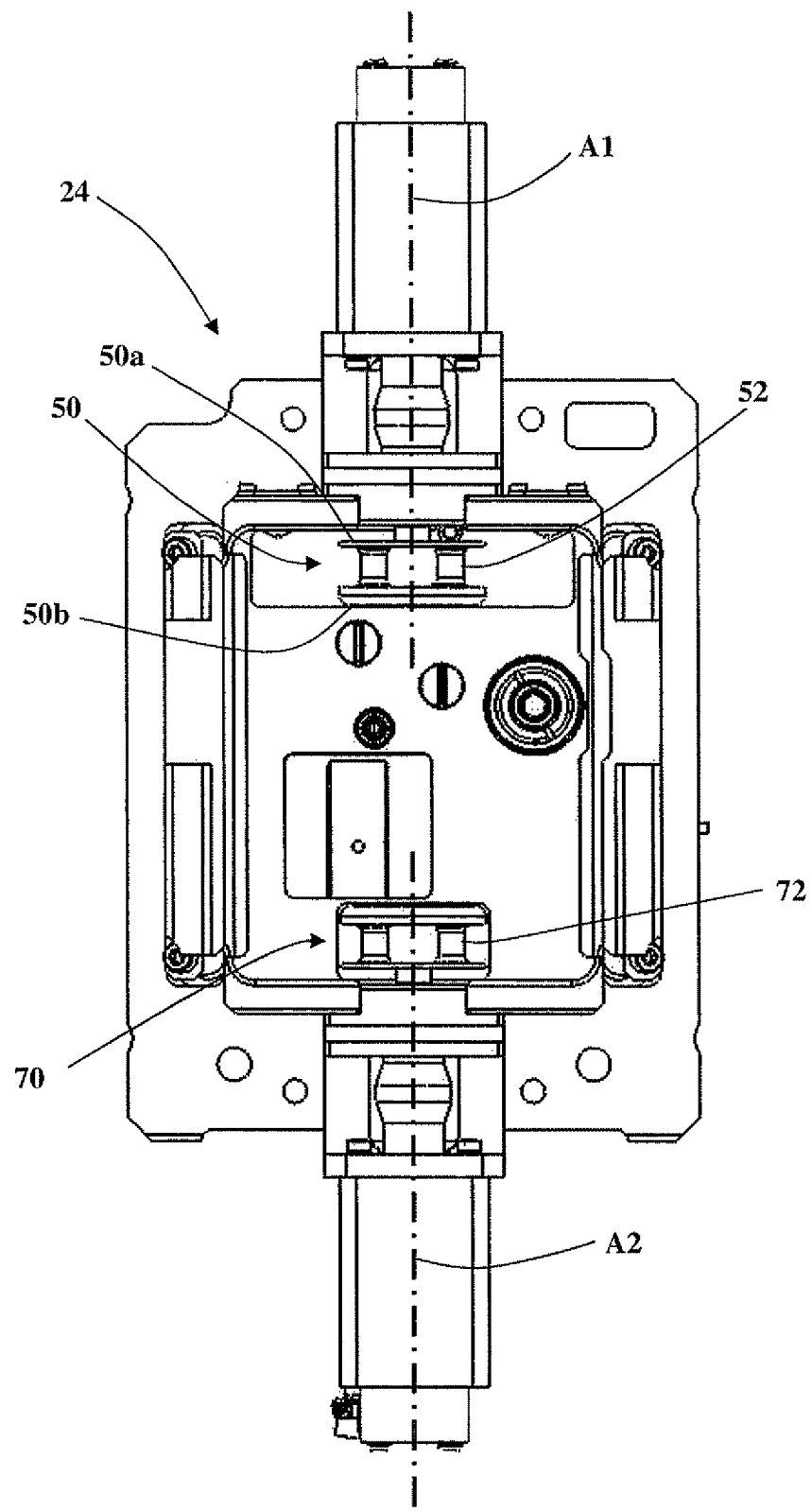
FIG. 5 is a front view of the surgical console shown in FIG. 4.
Figure 6:
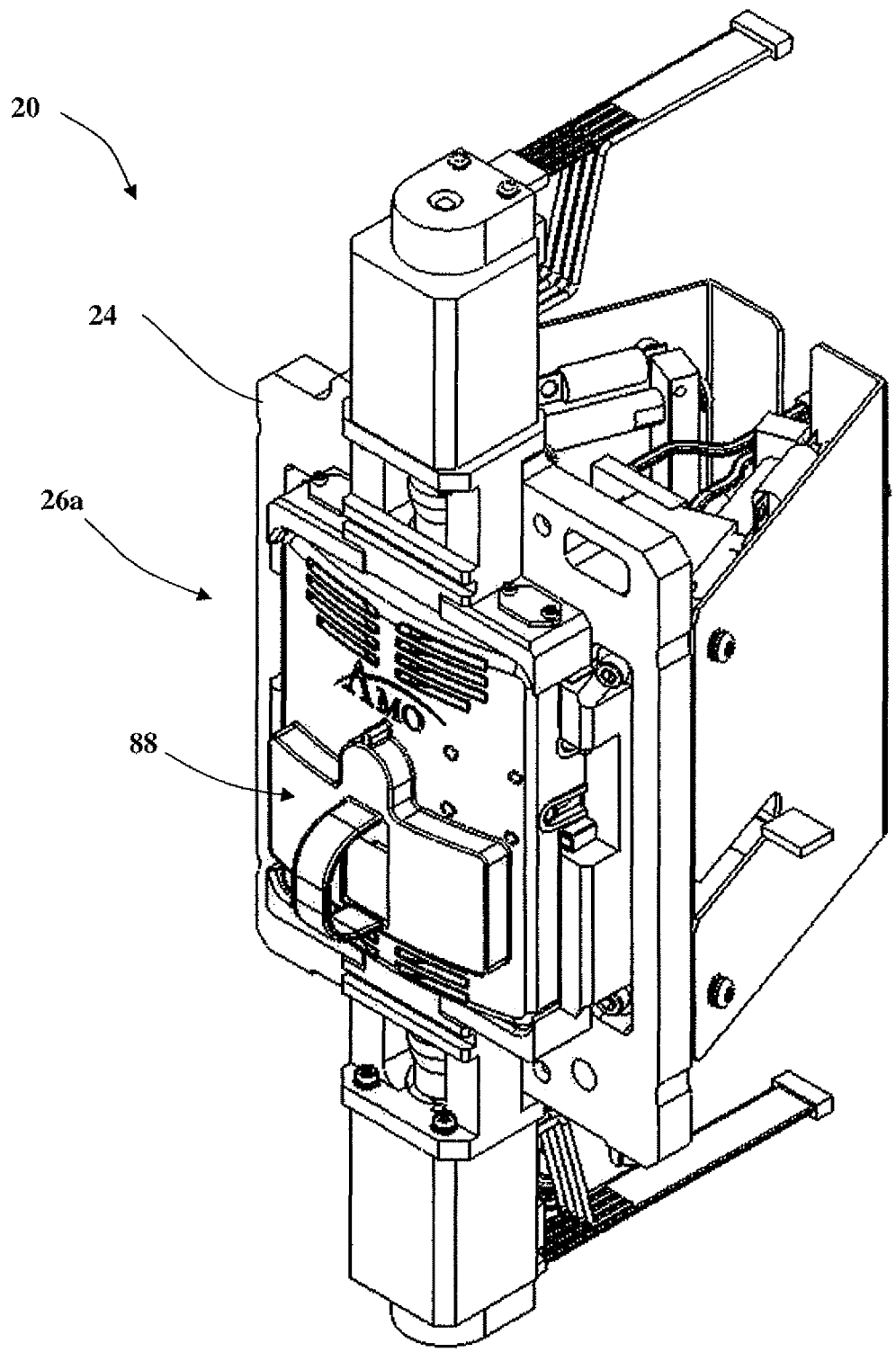
FIG. 6 is a perspective view of the surgical system illustrated in FIG. 4 showing the cassette coupled to the surgical console.

FIGS. 4-6 illustrate perspective and front views of a portion of the system 20 that is schematically illustrated in FIG. 2, illustrating various elements of the console 22 and the cassette 26a (or alternatively cassette 26b). For clarity, the handpiece 22 and the irrigation source 34 are not illustrated in the FIGS. 4-6. Referring to FIG. 4, the cassette 26 is shown separated from the console 24, while in FIG. 6 the cassette 26 is shown engaged with the console 24 so as to couple a handpiece or eye treatment probe with the console 24. FIGS. 4-6, illustrate various components of the console 24 and the cassette 26b, including the pump head 50 with the plurality of projections 52 thereof.

With particular reference to FIG. 5, the projections 52 may be attached at one of their ends to a drive plate 50a and configured to rotate about an axis A1. The projections may also be commonly joined at their opposite ends to an attachment plate 50b, for example, to increase rigidity. The console 24 may also include a second pump head 70 that can be used in the drain peristaltic pump 60. The second pump head 70 comprises projections, fingers, or rollers 72 that are configured to rotate about an axis A2. In the illustrated embodiment, the axes A1 and A2 are collinear; however, other relationships between the axes A1 and A2 are possible (e.g., the axes may be parallel to one another, orthogonal to one another, or coplanar).

Figure 7:
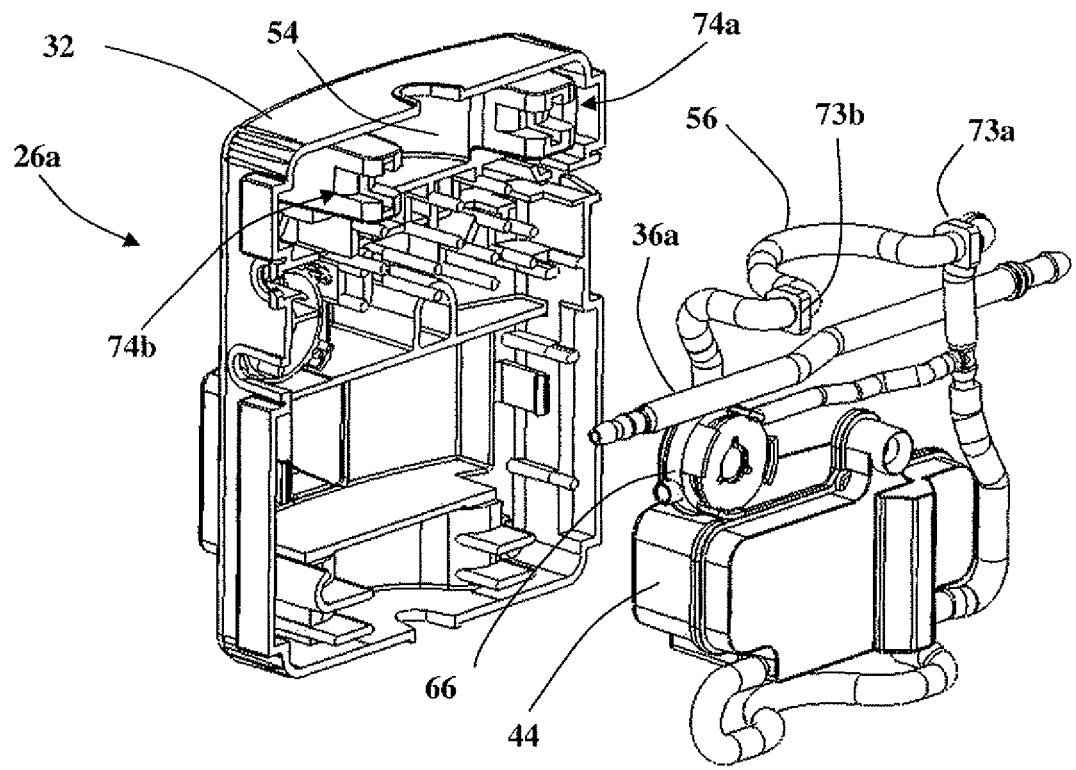
FIG. 7 is an exploded view of the cassette shown in FIG. 4.

FIG. 7 is an exploded view of the cassette 26a. Various components and fluid lines disposed within the cassette body 32 are clearly visible. In particular, the resilient channel 56 is seen in an uncompressed state and arcuately shaped to generally fit along the ramp 54 that is formed in the cassette frame 32. The fluid lines in the illustrated embodiment are in the form of flexible tubing; however, all or portions of the fluid lines of the cassette 26a (or 26b) may be replaced other types of channeling. For example, all or portions of the fluidic lines of the cassette 26a (or 26b) may be at least partially replaced by channels appropriately formed in a cassette frame. In some embodiments, the channels may be formed by the combination of the cassette frame 32 and a resilient cover, for example, as disclosed in U.S. Pat. No. 6,962,488.

Figure 8:
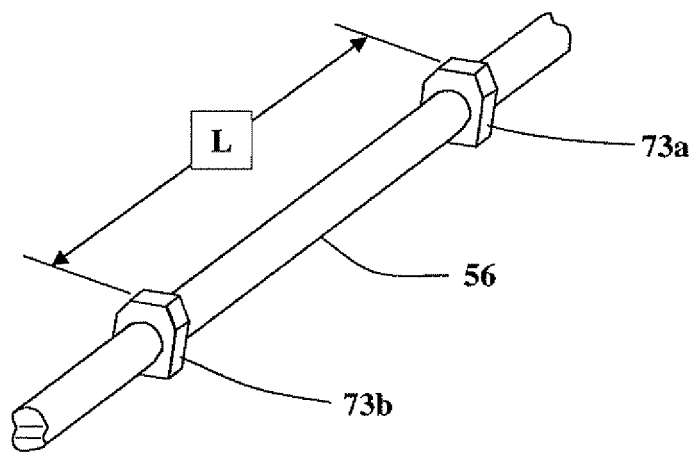
FIG. 8 is portion of a resilient channel shown in FIG. 7 in a straightened form.

In certain embodiments, the cassette 26a (or 26b) comprises first and second collars 73a, 73b that are disposed along the resilient channel 56. Referring to FIG. 8, which shows a portion of the resilient channel 56 in a straighten form prior to being configured for mounting in the cassette 26a (or 26b), the collars 73a, 73b are molded or otherwise attached to the resilient channel 56 so as to prevent slippage therebetween. The collars 73a, 73b may be separated by a predetermined distance L that is selected to provide efficient pump performance when the resilient channel 56 is mounted to the cassette, for example, by insertion into receivers 74a, 74b, respectively. In the illustrated embodiment, the receivers 74a, 74b are located on bosses between which the ramp 54 is disposed. In order to help prevent twisting of the resilient channel 56, the collars 73a, 73b may be keyed to provide a preferred orientation of the collars within the receivers 74a, 74b. The keyed collars 73a, 73b may be configured so that they can be mounted only in one orientation within the receivers 74a, 74b or may simply be shaped so that the correct orientation is evident upon visual inspection.

Figure 9:
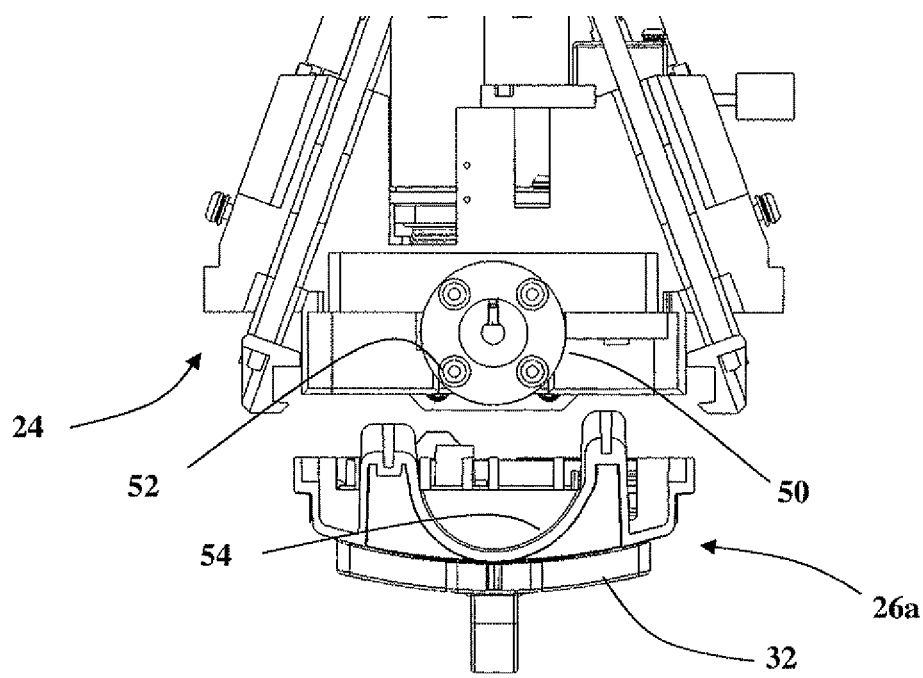
FIG. 9 is a top view of a portion of the surgical system shown in FIG. 4.
Figure 10:
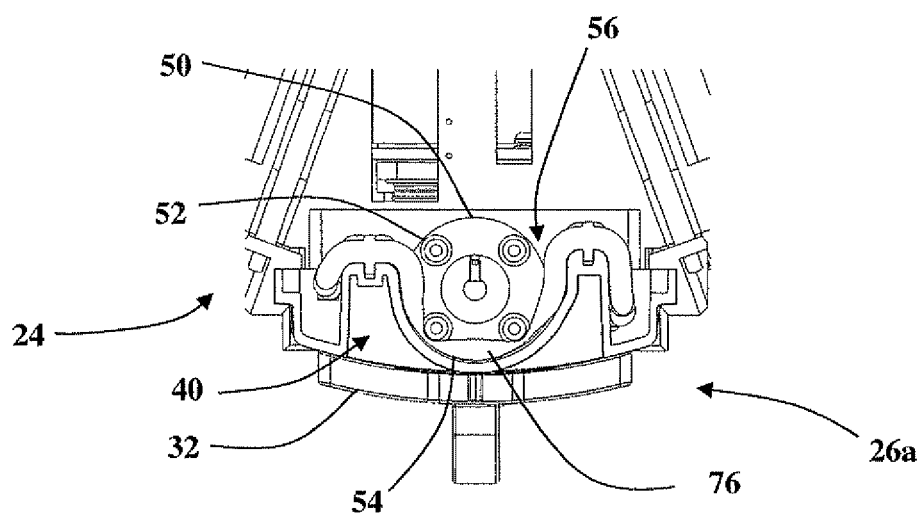
FIG. 10 is a top view of a portion of the surgical system shown in FIG. 4 illustrating the cassette coupled to the surgical console.

FIGS. 9 and 10 show cutaway top views of the console 24 and the cassette 26 particularly illustrating the relationship between the projections 52 of the head 50 and the ramp 54 formed in the cassette frame 32. For clarity, the resilient channel 56 is not shown in FIG. 9. In FIG. 10 the resilient channel 56 is shown compressed between the ramp 54 and two of the projections 52 of the pump head 50. The ramp 54 is configured to at least partially enclose at least some of the projections 52 when the cassette 26 is engaged with the console 24. As seen in FIG. 10, the aspiration pump 40 is formed by the engagement of the cassette 26 with the console 24. As the projections 52 rotate about the axis A1, fluid and other material is entrapped within a volume 76 of the resilient channel 56 and transferred from an inlet portion of the peristaltic pump 40 to an exit portion thereof. Since the resilient channel 56 is fluidly connected to the aspiration line 38, the material is transferred from the eye E and through the peristaltic pump 40 as the resilient channel 56 is repeatedly engaged by or squeezed between the ramp 54 and the plurality of projections 52. As discussed in greater detail below, the profile of the ramp 54 may be configured mitigate or substantially eliminate large and/or rapid variations in the pressure of the aspiration line 38 as each of the projections 52 initially engages and subsequently squeezes the resilient channel 56.

FIGS. 11 and 12 illustrate the cassette 26 with associated components of the system 20, including but not limited to, irrigation inlet and outlet lines 37a, 37b, aspiration line 38, waste bag 62, holding tank 44, and vacuum sensor 66. In other embodiments, the same cassette body 32 may be configured for use with only the aspiration peristaltic pump 40, as discussed in relation to the system schematically illustrated in FIG. 3. The irrigation and aspiration lines 37b, 38 are configured to be coupled to the handpiece 22, allowing the cassette 26 to provide at least irrigation fluid to, and aspiration of fluid from, the eye E. In some embodiments, the system 20 handpiece further comprises means for emulsification of the natural lens of the eye E. An ultrasonically driven piezoelectric crystal may be used to provide this function; however, other means are consistent with embodiments of the present invention, for example, a high energy laser beam. In other embodiments, the handpiece 22 is configured to cut and remove vitreous material in the posterior chamber of the eye E, for example, by including an electrically or pneumatically driven cutter blade.

Figure 13:
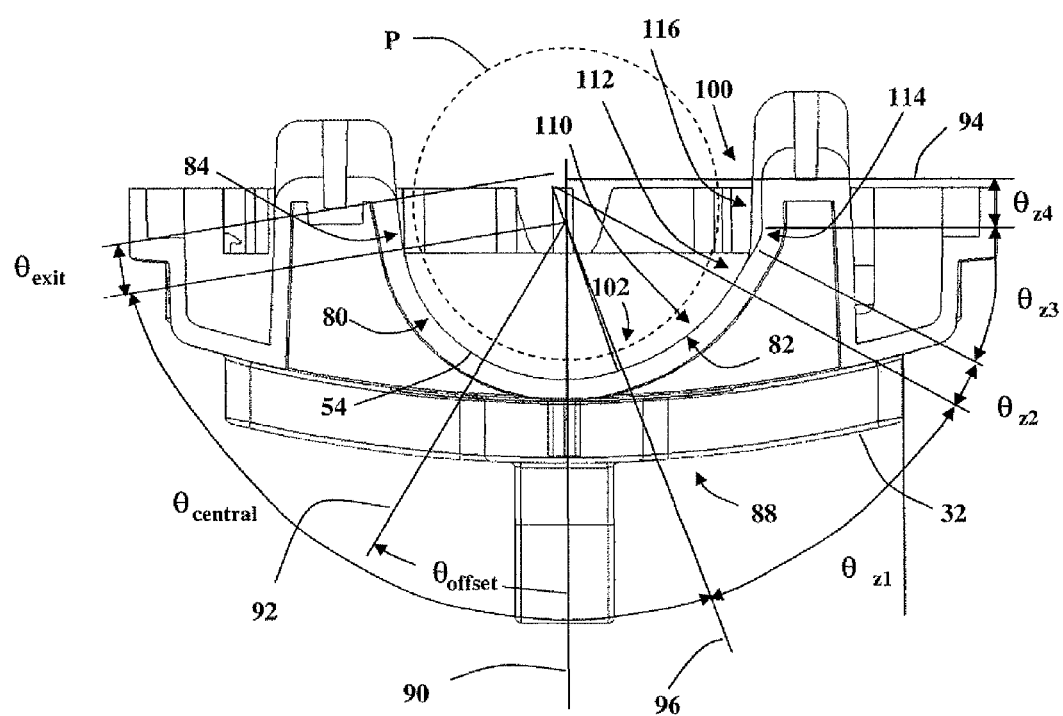
FIG. 13 is a top view of the cassette shown in FIG. 4 illustrating various feature of a ramp according to embodiments of the present invention that is configured to reduce pressure fluctuations at an input into a volumetric pump.
Figure 14:
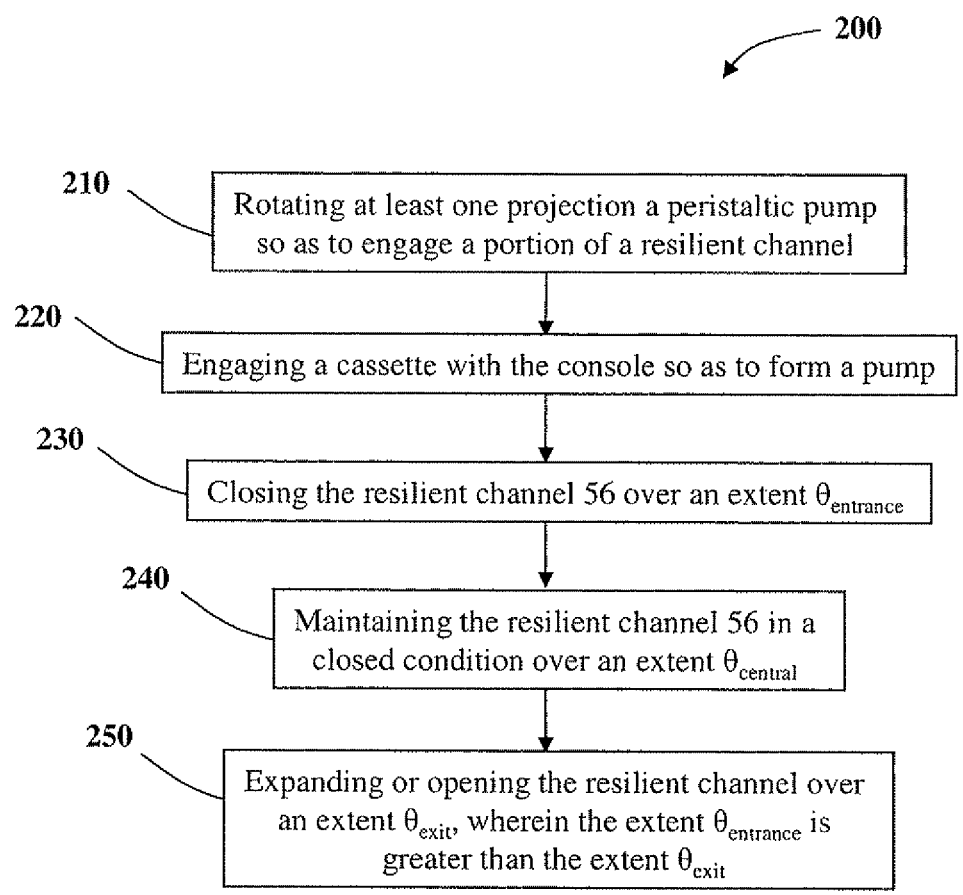
FIG. 14 is a block diagram of a method according to an embodiment of the present invention.
Figure 15A:
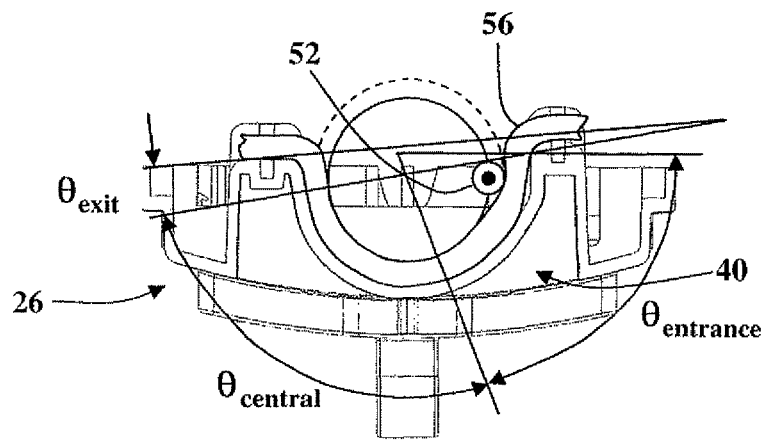
FIGS. 15A-15C are diagrams illustrating a method of operation of a pump according to embodiments of the invention.
Figure 15B:
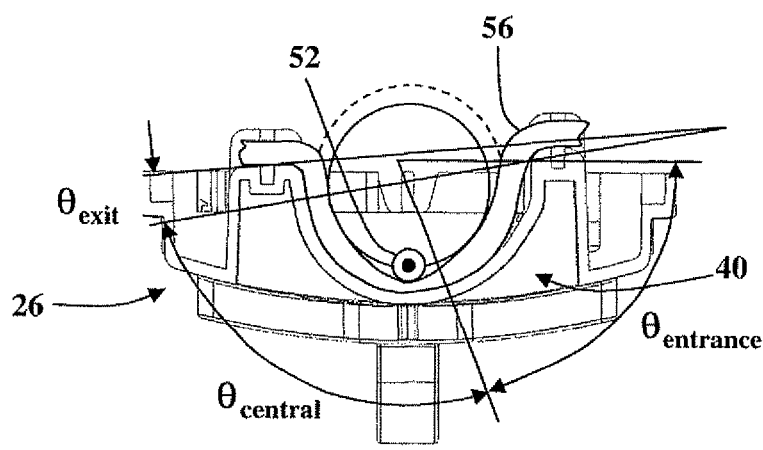
Figure 15C:
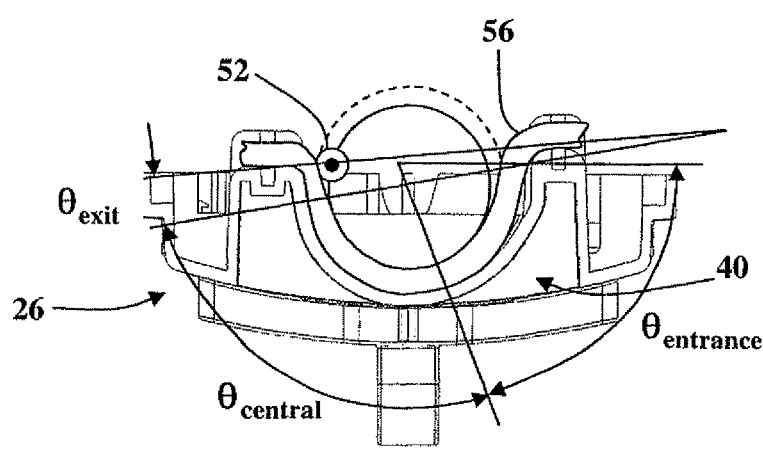

Referring to FIG. 13, in certain embodiments, the ramp 54 is configured to have an arcuate form that can reduce or substantially eliminate rapid and/or large pressure fluctuations in the aspiration line 38 and the eye E caused by the peristaltic pump 40. The dotted circle P illustrates an approximate path of the distal most portions of projections 52 (i.e., the point or line on each projection 52 that is closest to ramp 54 as the pump head 50 rotates). In such embodiments, the ramp 54 comprises a central portion 80 generally configured such that the resilient channel 56 is completely sealed or substantially sealed as the projections 52 rotate or move along the central portion 80 of the ramp 54. The shape of the central portion 80 may be characterized by a base curvature $C_{central}$ that is generally constant, although the shape of the central portion 80 may vary in accordance with particular design requirements or constraints.

The ramp 54 also comprises an entrance portion 82 having an arcuate extent over which one of the projections 52 closes the resilient channel 56 as the projections 52 move by the ramp 54. The entrance portion 82 may be characterized by a base curvature $C_{entrance}$ that is different from the base curvature $C_{central}$, preferably less than the curvature $C_{central}$. The decreased curvature $C_{entrance}$ of the entrance portion 82 may be configured to reduce the rate at which the resilient channel 56 is compressed, thus reducing or eliminating pressure fluctuations in the aspiration line 38 and eye E. In order to aid in the reduction of pressure fluctuations, the transition between entrance portion 82 and the central portion 80 is made generally smooth, for example, by configuring the entrance and central portions 82, 80 to be tangent at a connection point or line therebetween. The shape of the entrance portion 82 may have a constant curvature; however, as discussed in greater detail below, a more complex shape may advantageously further reduce pressure fluctuations at the entrance to the peristaltic pump 40.

The ramp 54 further comprises an exit portion 84 having an arcuate extent and characterized by a base curvature $C_{exit}$ that is different from the base curvature $C_{central}$. The shape of the exit portion 84 may have a constant curvature, although the shape may vary in accordance with particular design requirements or constraints. Advantageously, the extent of the entrance portion 82 is unequal to the extent of the exit portion 84. In the illustrated embodiment, the entrance portion 82 has a greater extent than that of the exit portion 84, for example, to provide a greater time and distance over which the resilient channel 56 is gradually squeezed or compressed. By increasing the extent of the entrance portion, the rate at which resilient channel 56 is compressed may be decreased, thus allowing the pressure fluctuations in the aspiration line 38 to be reduced.

In some embodiments, the smaller extent of the exit portion 84 produce a relatively large or rapid pressure increase at the exit of the pump 40 and the resilient channel 56. In general, this will not cause problems, since the exit of the resilient channel is isolated from the aspiration line 38 and the eye E. In some instance, however, the entrance portion 82 may actually have a smaller extent than that of the exit portion 84, depending upon the choices of a particular designer.

As illustrated in FIG. 13, the extent of the portions 80, 82, 84 may have generally arcuate extents. These arcuate extents may be approximately centered about center of the dotted circle P, although it will be appreciated that portions of the portions 80, 82, 84, particularly of the entrance portion 82, may have very large radii of curvature (even infinite) that are centered at great distances from the center of the dotted circle P. In some embodiments, the pump 40 may be linear or substantially linear in its operation, in which case the extent of one or more of the portions 80, 82, 84 may be partially or substantially linear in nature or have very large radii of curvature.

Again referring to FIG. 13, exit portion 84 of the ramp 54 has an arcuate or angular extent $\theta_{exit}$. In some embodiments, the exit portion 84 is substantially linear, in which case the extent is more appropriately expressed as an linear distance, rather than an angular extent. The central portion 80 of the ramp 54 has an arcuate or angular extent $\theta_{central}$ that preferably is much greater than $\theta_{exit}$. Generally, the angular extent of the central portion 80 is at least 90 degrees in order that at least two of the projections 52 of the peristaltic pump 40 close the resilient channel 56 at any given time or position of the pump head 50. In some embodiments, the angular extent $\theta_{central}$ is 100 degrees or about 100 degrees, for example, when the pump head has four projections 52 that are approximately 90 degrees apart from one another. In other embodiments, the angular extent $\theta_{central}$ is between about 90 degrees and about 120 degrees. In yet other embodiments, the angular extent $\theta_{central}$ may be less than about 90 degrees, for example, when the pump head has five, six, or more projections 52 that are approximately evenly space apart from one another. Alternatively, the angular extent $\theta_{central}$ may be greater than 120 degrees, 130 degrees, or even 140 degrees, for example, when the pump head has two or three projections 52 that are approximately evenly space apart from one another.

The entrance portion 82 of the ramp 54 has a substantially arcuate extent from line 94 to line 96 shown in FIG. 13. The entrance portion 82 comprises a proximal portion 100 near the entrance into the pump 40 (e.g., at or near the intersection of the ramp 54 with the line 94) and a distal portion 102 near the central portion 82 of the ramp 54 (e.g., disposed at or near the intersection of the ramp 54 profile with the line 96). The profile of entrance portion 82 generally moves progressively further from the circle P when moving from the proximal portion 100 to the distal portion 102. In general, proximal portion 100 is disposed farther away from the circle P than the distal portion 102. In some embodiments, proximal portion 100 is configured such that when the projections 52 of the pump 40 initially engage the resilient channel 56, the resilient channel 56 moves away from the circle P and/or toward the proximal portion 100 of the ramp 54. This may advantageously reduce or eliminate the production of pressure waves or variations in the aspiration line 38 that might otherwise damage the eye E.

The entrance portion 82 of the ramp 54 may comprise adjoining first segment 110, second segment 112, third segment 114, and fourth segment 116. Each of the segments 110, 112, 114, 116 may have a curvature that is constant over most of their extents and may include relatively small transition portions between each of the segments for providing smooth transitions therebetween. Alternatively, one or more of the segments 110, 112, 114, 116 may comprise a non-circular profile, for example, a profile that varies slightly from a base curvature with a predetermined radius of curvature. In the illustrated embodiment, the second segment 112 has a curvature that is less than that of the first segment 110. In some embodiments, the second segment 112 has a curvature of zero (e.g., a straight line) or nearly zero (e.g., a very large radius of curvature). The first and/or second segments 110, 112 may be configured to provide a predetermined location of the proximal portion 100, so as to provide a desired interaction between the resilient channel 54 and the projections 52 upon engagement therebetween. The third segment 114 has a relatively large curvature that is greater than that of the second segment 112. The third segment 114 may be configured provide a predetermined orientation of the proximal portion 100. The fourth segment 116 has curvature that is less than the curvature of the second segment, and is preferably straight, nearly straight, or only slightly arcuate in shape.

In some embodiments, the cassette housing 32 comprises a front face 88 that is substantially symmetrically disposed about a central axis or perpendicular plane. Thus, the front face 88 is substantially normal to a first axis 90, while the central portion 80 is asymmetrically disposed about the first axis 90. In addition, the central portion 80 may be symmetrically disposed about a second axis 92 that itself is disposed at an angle $\theta_{offset}$ relative to the first axis 90 (where positive angles in FIG. 13 are in a clockwise direction from the first axis 90). In the illustrated embodiment, the angular extent $\theta_{central}$ of the central portion 90 is about 100 degrees and $\theta_{offset}$ is about 30 degrees. Generally, the angle $\theta_{offset}$ is between about −40 degrees and about +40 degrees, preferably between −30 degrees and +30 degrees. When the entrance portion 82 is configured to have an extent that is greater than that of the exit portion 84, $\theta_{offset}$ is between about 0 degrees and about 50 degrees, preferably between about 20 degrees and about 40 degrees. The ranges may, of course, change depending on the particular design parameters, for example, the number of projections 52 in the head 50 of the pump 40.

Referring to FIGS. 14 and 15A-C a method 200 of operating the surgical treatment system 20 comprises an operational block 210 of engaging a cassette according to embodiments of the present invention (e.g., one of the cassettes 26, 26a, or 26b) with the console 24 so as to form the pump 40 and to couple the handpiece 22 with the console 24. The method 200 also comprises an operational block 220 of rotating at least one projection 52 of the peristaltic pump 40 so as to engage a portion of the resilient channel 56. The method 200 additionally comprises an operational block 230 of compressing or closing the resilient channel 56 over an extent $\theta_{entrance}$ so as to draw in fluid and/or other material inside the resilient channel 56. The method 200 further comprises an operational block 240 of maintaining the resilient channel 56 in a sealed or closed condition over an extent $\theta_{central}$. The method 200 also comprises an operational block 250 of expanding or opening the resilient channel 56 over an extent $\theta_{exit}$ so as to allow material to be ejected from the peristaltic pump 40, wherein the extent $\theta_{entrance}$ is greater than the extent $\theta_{exit}$.

The above presents a description of the best mode contemplated of carrying out the present invention, and of the manner and process of making and using it, in such full, clear, concise, and exact terms as to enable any person skilled in the art to which it pertains to make and use this invention. This invention is, however, susceptible to modifications and alternate constructions from that discussed above which are fully equivalent. Consequently, it is not the intention to limit this invention to the particular embodiments disclosed. On the contrary, the intention is to cover modifications and alternate constructions coming within the spirit and scope of the invention as generally expressed by the following claims, which particularly point out and distinctly claim the subject matter of the invention.

What is claimed is:

1. A fluidics cassette, comprising:
   a housing;
   an irrigation line and an aspiration line, the lines configured to provided irrigation and aspiration functions for an eye treatment probe;
   a ramp configured for transferring fluid through a resilient channel when the resilient channel is engaged between the ramp and one or more of a plurality of projections of a pump head, the ramp comprising:
      a central portion characterized by a first base curvature at which the resilient channel is completely sealed as the plurality of projections rotate along the central portion;
      an entrance portion characterized by a second base curvature that is different from the first base curvature and having an extent over which one of the projections closes the resilient channel as the projection moves by the ramp; and
      an exit portion characterized by a third base curvature that is different from the first base curvature and having an extent less than that of the entrance portion for producing a rapid pressure increase;
   wherein the second base curvature of the entrance portion being unequal to the third base curvature of the exit portion, wherein the portion of the ramp that is configured to engage the pump head has an arcuate shape from a beginning of the entrance portion through the central portion to an end of the exit portion.

2. The fluidics cassette of claim 1, wherein the resilient channel is disposed within the aspiration conduit.

3. A fluidics cassette, comprising:
   a housing comprising a front face disposed substantially normal to a first axis;
   an irrigation conduit and an aspiration conduit, the conduits configured to provided irrigation and aspiration functions for an eye treatment probe;
   a ramp configured for transferring fluid through a resilient channel when the resilient channel is engaged between the ramp and one or more of a plurality of projections of a pump head, the ramp comprising:
      a central portion characterized by a first base curvature at which the resilient channel is completely sealed as the plurality of projections rotate along the central portion;
      an entrance portion characterized by a second base curvature that is different from the first base curvature and having an extent over which one of the projections closes the resilient channel as the projection moves by the ramp;
      the central portion being asymmetrically disposed about the first axis.

4. The fluidics cassette of claim 3, wherein the central portion is symmetrically disposed about a second axis, the second axis disposed at a predetermined angle relative to the first axis.

5. The fluidics cassette of claim 4, wherein the central portion has an arcuate extent of about 100 degrees and the predetermined angle is about 30 degrees.

6. The fluidics cassette of claim 3, wherein the front face is disposed substantially symmetrically about the first axis.

7. A fluidics cassette, comprising
   a housing;
   an irrigation conduit and an aspiration conduit, the conduits configured to provided irrigation and aspiration functions for an eye treatment probe;
   a resilient tube configured to transfer fluid from when engaged by a plurality of projections of a pump head;
   a first keyed insert disposed along an input portion of the resilient tube;
   a second keyed insert substantially congruent with the first keyed insert and disposed along an output portion of the resilient tube;
   a first keyed receiver coupled with the housing; and
   a second keyed receiver coupled with the housing;
   wherein the first keyed insert and second keyed insert having the same orientation when the tube is in an unstressed condition; and
   wherein the first and second keyed inserts being configured to orient the resilient tube with a ramp when coupled with the first keyed receiver and the second keyed receiver,
   wherein the first and second keyed inserts each have a shape and the first and second keyed receivers each have an internal shape that corresponds to the shape of their respective keyed inserts, and
   wherein the first and second keyed inserts are configured to only couple with the first and second keyed receivers in a single orientation.

8. A fluidics cassette of claim 7, further comprising a ramp configured for transferring fluid through the resilient tube as the projections move by the ramp.

9. A fluidics cassette of claim 7, wherein the housing comprises a pair of cavities disposed to receive the first keyed insert and the second keyed insert.

10. A fluidics cassette of claim 9, wherein the spacing between the first keyed insert and the second keyed insert is selected to provide a predetermined tension of the resilient tube as the projections move by the ramp.

11. The fluidics cassette of claim 1, wherein the second base curvature is less than the first base curvature.

* * * * *